(12) United States Patent
Bhavnani

(10) Patent No.: US 7,503,476 B2
(45) Date of Patent: Mar. 17, 2009

(54) PEDOMETER AND METHOD OF ADVERTISING

(75) Inventor: Dilip Bhavnani, Beverly Hills, CA (US)

(73) Assignee: Sun Coast Merchandise Corporation, Commerce, CA (US)

( * ) Notice: Subject to any disclaimer, the term of this patent is extended or adjusted under 35 U.S.C. 154(b) by 0 days.

(21) Appl. No.: 11/008,304

(22) Filed: Dec. 8, 2004

(65) Prior Publication Data
US 2007/0017967 A1    Jan. 25, 2007

(51) Int. Cl.
*G01C 22/00*    (2006.01)
(52) U.S. Cl. .................. 235/105; 377/24.2; 702/160
(58) Field of Classification Search ............... 235/105, 235/487, 104, 235–377; 377/24.2; 702/160
See application file for complete search history.

(56) References Cited

U.S. PATENT DOCUMENTS

| | | | |
|---|---|---|---|
| 4,322,609 A | | 3/1982 | Kato |
| 4,367,752 A * | | 1/1983 | Jimenez et al. ............ 600/502 |
| 4,566,461 A * | | 1/1986 | Lubell et al. ............... 600/481 |
| 4,855,942 A * | | 8/1989 | Bianco ....................... 702/160 |
| 6,013,007 A * | | 1/2000 | Root et al. ..................... 482/8 |
| 6,135,951 A * | | 10/2000 | Richardson et al. ......... 600/300 |
| 6,349,126 B2 * | | 2/2002 | Ogawa et al. .............. 377/24.2 |
| 7,229,385 B2 * | | 6/2007 | Freeman et al. ................ 482/4 |
| 2002/0019296 A1 * | | 2/2002 | Freeman et al. ................ 482/4 |
| 2004/0140348 A1 * | | 7/2004 | Fromm ....................... 235/105 |
| 2005/0195094 A1 * | | 9/2005 | White ................... 340/870.01 |

* cited by examiner

*Primary Examiner*—Seung H Lee
(74) *Attorney, Agent, or Firm*—The Soni Law Firm

(57) ABSTRACT

A compact multifunction pedometer and method of advertising includes a computerized calculating function to accurately determine the calorie consumption, distance and the time for exercise duration. Utilizing input data of the user's height, weight, average stride and desired time period for exercise of walking or running, the pedometer calculates, and if desired displays, the consumed calories as well as the distance traveled and lapsed time of striding or alternatively, the time remaining for a scheduled walking or running session. The calories burned during exercise are accurately determined through calculations based on the individual's stride and weight data input by the user. The pedometer is extremely compact, has easy to operate function controls and may include a belt clip for ease of use during exercise. The pedometer including surfaces suitable for displaying advertising.

7 Claims, 3 Drawing Sheets

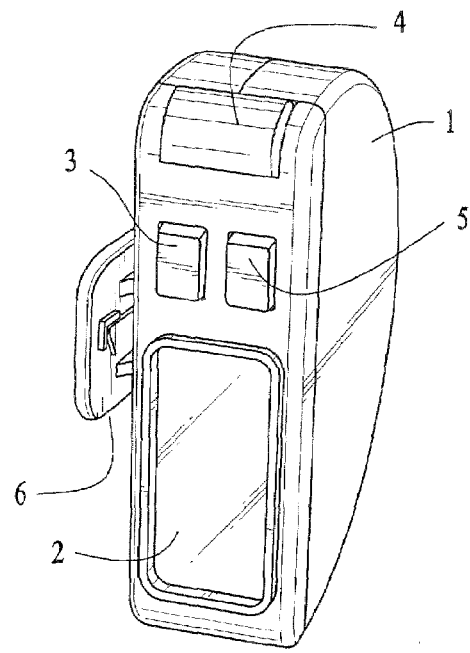 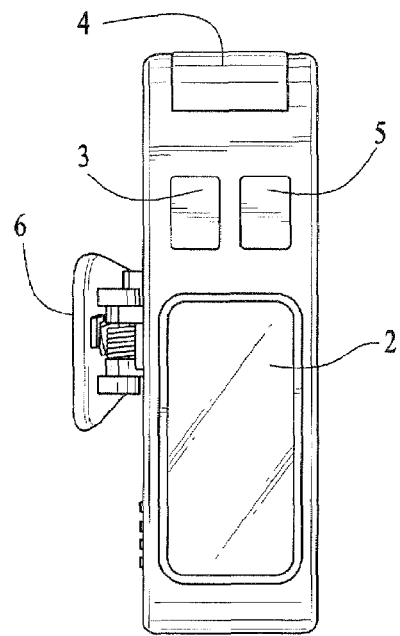
fig.1   fig.2
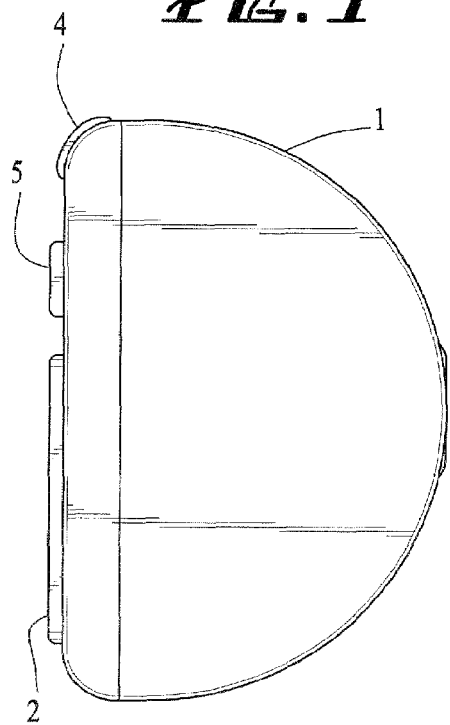 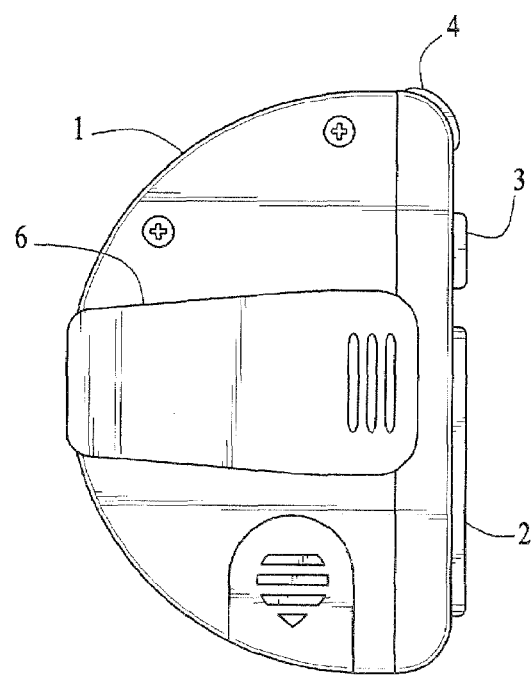
fig.3   fig.4

PEDOMETER AND METHOD OF ADVERTISING

BACKGROUND OF THE INVENTION

1. Field of the Invention

The present invention relates to a multifunction pedometer. More specifically, the present invention relates to a pedometer that includes functions to determine the distance traveled, the time elapsed or remaining, and the caloric consumption during the wearer's exercise session. The present invention also includes surfaces for displaying advertising.

2. Description of the Prior Art

A variety of pedometers are well known in the prior art. U.S. Pat. No. 4,322,609 to Kato describes a pedometer which utilizes pendulum type action to determine the steps taken by the user. From only this approximation, the Kato pedometer then estimates the calories burned based only upon the number of repetitions of the pedometer pendulum.

Similarly, U.S. Pat. No. 4,855,942, to Bianco describes a pedometer which relies upon the individual's input data of stride, age, sex and weight to estimate the distance traveled as well as the calories burned.

What is lacking in the existing art is a calculation and display device which is capable of many concurrent functions. In any exercise regimen, the time of exercise is critical and is directly related to the distance traveled and the calories burned. Moreover, what is lacking in the existing art is a device and a method by which the wearer of a pedometer may be continuously advised by means of a visual display as to the time lapsed or remaining for an exercise period, the distance traveled and the cumulative calories burned during the interval. Having such a multifunction device would enable the user to readily monitor their exercise regimen and quickly determine the time required to achieve a desired calorie burn. Moreover, the user could easily determine their progress in frequent and regular exercising, and if necessary or desired, alter the pace, time or other variables included therein so as to improve their performance, stamina or other desired physical characteristics. Also missing in the prior art is a pedometer which serves as an advertising or an advertising devise which is also a multi-function pedometer.

SUMMARY OF THE INVENTION

An object of the present invention to provide a multifunction device which continuously calculates and displays important numerical values for the wearer to observe during a walking or running exercise regimen. One key feature of the present invention is its calculation function which continually calculates and displays the calories burned by an individual during walking or running for a desired period of time. This calculation is based upon the calories burned as required to move a particular mass at a particular speed over the duration of a specific time interval.

Still another object of this invention is to provide a means and a method by which the wearer of the invention may continuously monitor his or her caloric performance during a specified time interval as well as monitor distance traveled, the time lapsed or alternatively, the time remaining for such a given time interval.

The objects of this invention are accomplished by incorporating a timing function and a caloric consumption calculation within the pedometer, which performs a number of concurrent purposes. First, the timing function is utilized to approximate the speed at which the individual is walking or running by calculating the distance traveled during a time interval. This numerical value is then further utilized in the caloric consumption calculation. Additionally, the timing function is used to input the total time for which the user wishes to walk or run and thereafter, continuously calculating and displaying the time lapsed during the exercise period, or alternatively, the time remaining for the duration of the exercise period.

An additional object of the present invention is to provide a means and method for advertising or promotion by utilizing imprinted advertising or graphical material on at least one outwardly facing surface of the pedometer.

BRIEF DESCRIPTION OF THE DRAWINGS

FIG. 1 is a perspective view of a pedometer;

FIG. 2 is a front elevational view of the pedometer of FIG. 1;

FIG. 3 is a right side elevational view of the pedometer of FIG. 1;

FIG. 4 is a left side elevational view of the pedometer of FIG. 1;

DETAILED DESCRIPTION OF THE INVENTION

Figures 5, 6:
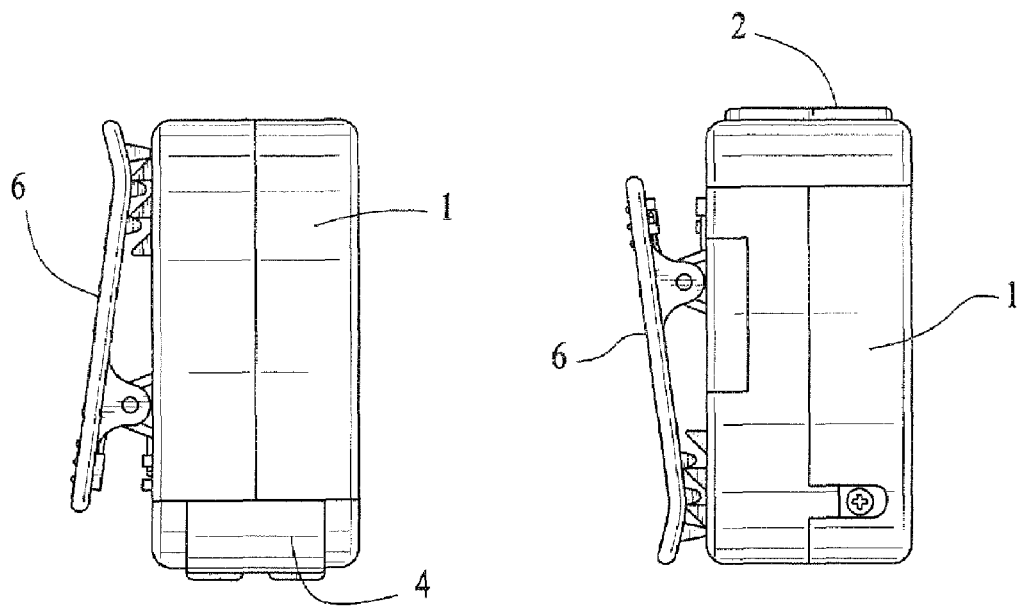
FIG. 5 is a top plan view of the pedometer of FIG. 1.
FIG. 6 is a bottom plan view of the pedometer of FIG. 1.

As shown in FIG. 1, the preferred embodiment of the present invention contemplates a multifunction pedometer which is compact size and may be easily used by an individual to monitor and display important criteria of an exercise program of walking or running. The invention includes an housing (1), which encloses the electronic components, primarily a microprocessor (100) disposed in the housing (1) electrically connected to a memory unit (102), timer (108) and step counter (106), the microprocessor (100) configured to receive inputted numerical values therefrom, the time elapsed after start of exercise, and total number of steps by the user. A set of input controls (104) is disposed on the housing (1) for manually inputting a fixed numerical value for each of a user's height, weight, and stride length, and for a desired exercise time interval. The memory unit (102) is disposed within the housing (1) and electrically connected to the input controls (104) for storing fixed numerical values therein. The step counter (106) is disposed within the housing (1) for measuring total number of steps by the user during the time elapsed after start of exercise. The microprocessor (100) is preferably programmed and limited to selectively calculate a linear ambulatory distance traveled by the user during the time elapsed after start of exercise solely from the inputted Fixed numerical value of the user's stride length and the total number of steps, total calories burned by the user during the time elapsed after start of exercise solely from the inputted fixed numerical value of the user's weight and the total number of steps, and remaining time for exercise solely from the inputted fixed numerical value of the desired exercise time interval and the time elapsed after start of exercise. These electronic components, such as the microprocessor (100), calculate the calories burned over time, the elapsed time and the time remaining for a specified time interval. The microprocessor (100) may incorporate a timer or may be used in conjunction with a timer (108) that is also enclosed within the pedometer housing (1). A power supply (110) is disposed within the housing (1) for supplying power to the input controls (104), the memory unit (102), the timer (108), the step counter (106), and the microprocessor (100).

These calculations are determined by calculations based upon the data input by the user, which consists of his or her weight, height, stride, and desired time for exercise. Once the stride is input, the microprocessor (100) calculates the time lapsed or remaining based on a subtraction function. With the input of the user's physical characteristics, the microprocessor (100) will calculate the caloric consumption based on the calories consumed being equal to the weight multiplied by the steps taken multiplied by a varying constant. As the wearer's walking or running speed increases, as calculated by the stride over a given time, this varying constant will also increase. For example, at a speed of less than 16 steps over 10 seconds, the caloric consumption formula is:

Calories Burned=weight (lbs)×(step for 10 seconds× 0.0002268);

whereas at a ambulatory speed in excess of 16 steps over 10 seconds, the formula becomes:

Calories Burned=weight (lbs)×(step for 10 seconds× 0.0005897−0.005715)

A microprocessor to perform calculations such as these is well known to those skilled in the art.

The preferred embodiment as shown in FIGS. 1 through 4 further includes a display (2) for which the user may select to display the calories burned, distance traveled, time lapsed or time remaining, by pressing the mode control (3). By selectively and sequentially pressing the mode control (3), the start/set button (4) and the input button (5) or input control (104) as directed by a command sequence, the user can calibrate and initiate the pedometer calculations by inputting his or her weight, height, stride and desired time interval for an exercise period.

Figure 7:
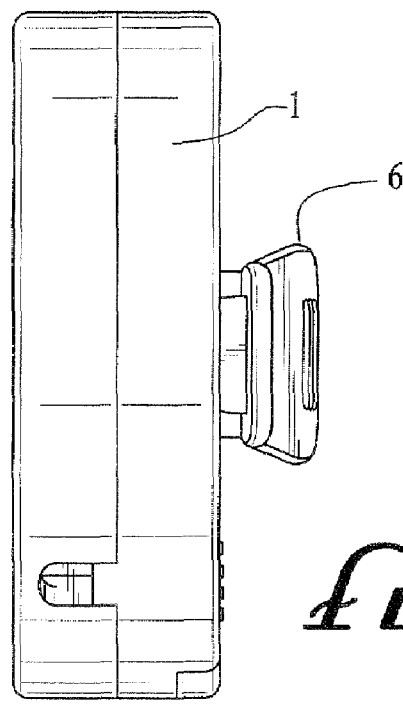
FIG. 7 is a rear elevational view of the pedometer of FIG. 1.
Figure 8:
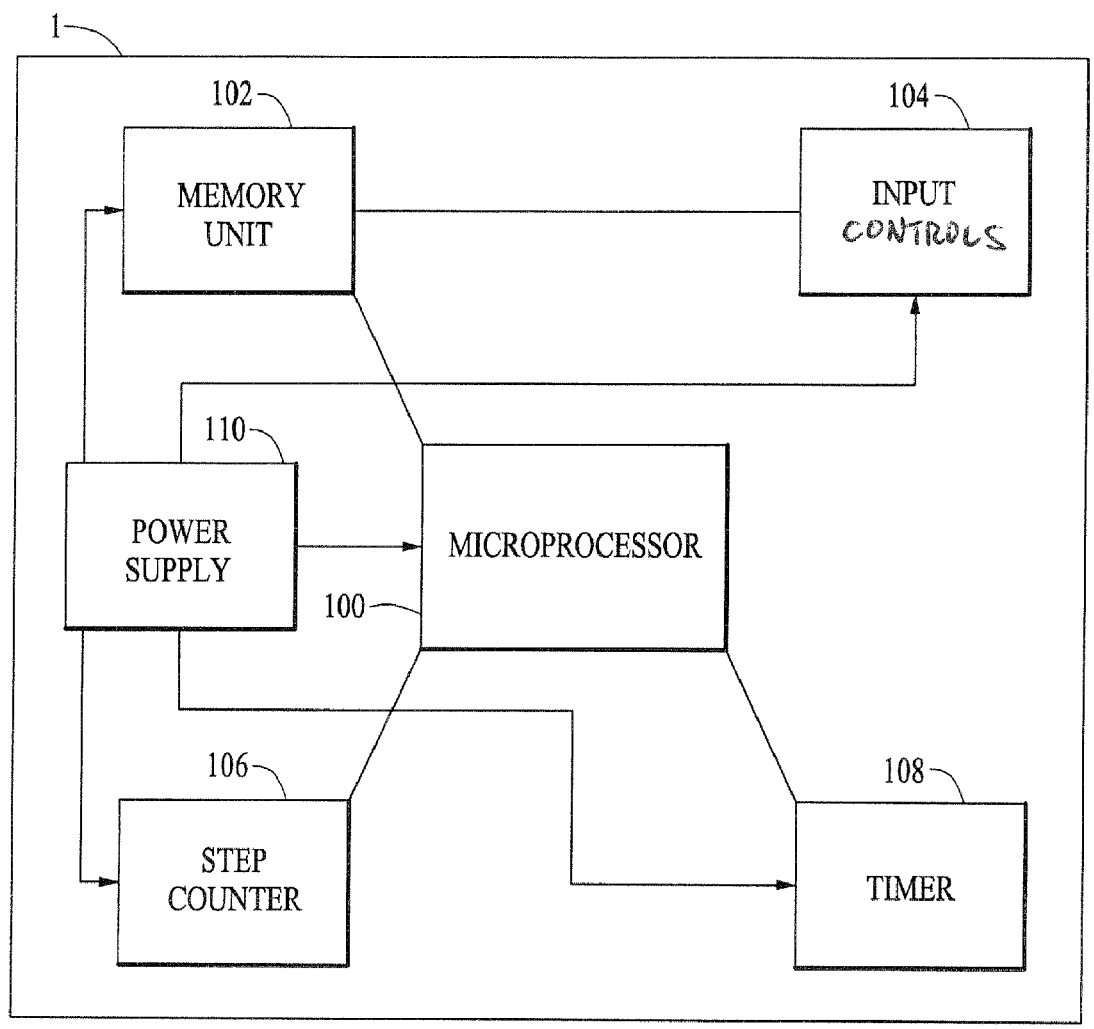
FIG. 8 is a schematic diagram of the electronic components of the pedometer of FIG. 1.

The preferred embodiment of the pedometer further includes a belt clip (6), as shown in FIGS. 1, 2, and 4-7, to enable the user's hands free operation of the pedometer and to permit the pedometer to be positioned at waist or belt level so as to be conveniently yet unobtrusively located during the exercise routine. By sequentially pressing the mode control (3), the user may selectively display any of the above described output values, including the distance traveled, the time lapsed, time remaining or the calories burned since commencing walking or running for the specific input time period.

What is claimed is:

1. A pedometer comprising:
a handheld housing;
a set of input controls disposed on the housing for manually inputting a fixed numerical value for each of a user's height, weight, and stride length, and for a desired exercise time interval;
a memory unit disposed within the housing and electrically connected to the input controls for storing the fixed numerical values;
a timer disposed within the housing for measuring time elapsed;
a step counter disposed within the housing for measuring total number of steps by the user during the time elapsed after start of exercise;
a microprocessor disposed within the housing and electrically connected to the memory unit, the timer, and the step counter, the microprocessor being configured to receive the inputted numerical values therefrom, the time elapsed after start of exercise, and the total number of steps by the user, wherein the microprocessor is programmed and limited to selectively calculate a linear ambulatory distance traveled by the user during the time elapsed after start of exercise solely from the inputted fixed numerical value of the user's stride length and the total number of steps, total calories burned by the user during the time elapsed after start of exercise solely from the inputted fixed numerical value of the user's weight and the total number of steps, and remaining time for exercise solely from the inputted fixed numerical value of the desired exercise time interval and the time elapsed after start of exercise; and
a power supply disposed within the housing for supplying power to the input controls, the memory unit, the timer, the step counter, and the microprocessor.

2. The pedometer of claim 1 further comprising a display screen that continuously displays at least one of the distance traveled by the user and the calories burned by the user.

3. The pedometer of claim 2, wherein the display screen further continuously displays one of the time interval elapsed and the time remaining.

4. The pedometer of claim 1 wherein the power supply is a battery.

5. The pedometer of claim 1 further comprising a belt clip disposed on a portion thereof.

6. The pedometer of claim 1 further including printed or graphical imprinting on a surface of the pedometer for the purpose of advertising or promotion.

7. A method of advertising comprising the steps of:
a) providing a pedometer comprising:
a handheld housing,
a set of input controls disposed on the housing for manually inputting a fixed numerical value for each of a user's height, weight, and stride length, and for a desired exercise time interval,
a memory unit disposed within the housing and electrically connected to the input controls for storing the fixed numerical values,
a timer disposed within the housing for measuring time elapsed,
a step counter disposed within the housing for measuring total number of steps by the user during the time elapsed after start of exercise,
a microprocessor disposed within the housing and electrically connected to the memory unit, the timer, and the step counter, the microprocessor being configured to receive the inputted numerical values therefrom, the time elapsed after start of exercise, and the total number of steps by the user, wherein the microprocessor is programmed to selectively calculate a linear ambulatory distance traveled by the user during the time elapsed after start of exercise solely from the inputted fixed numerical value of the user's stride length and the total number of steps, total calories burned by the user during the time elapsed after start of exercise solely from the inputted fixed numerical value of the user's weight and the total number of steps, and remaining time for exercise solely from the inputted fixed numerical value of the desired exercise time interval and the time elapsed after start of exercise,
a power supply disposed within the housing for supplying power to the input controls, the memory unit, the timer, the step counter, and the microprocessor; and
b) disposing advertising material on a visible outer surface of the pedometer.

* * * * *